US009823186B2

(12) United States Patent
Ochrombel

(10) Patent No.: US 9,823,186 B2
(45) Date of Patent: Nov. 21, 2017

(54) METHOD FOR DETECTING THE PRESENCE OR ABSENCE OF AN OPHTHALMIC LENS, IN PARTICULAR A CONTACT LENS, WITHIN A RECEPTACLE

(71) Applicant: Novartis AG, Basel (CH)

(72) Inventor: Rene Ochrombel, Bergheim (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/848,799

(22) Filed: Sep. 9, 2015

(65) Prior Publication Data

US 2016/0069796 A1    Mar. 10, 2016

Related U.S. Application Data

(60) Provisional application No. 62/047,693, filed on Sep. 9, 2014.

(51) Int. Cl.
G01N 21/3563 (2014.01)
G01N 21/3577 (2014.01)
G01V 8/12 (2006.01)
B65B 25/00 (2006.01)
B65B 57/10 (2006.01)
(Continued)

(52) U.S. Cl.
CPC ....... *G01N 21/3563* (2013.01); *B65B 25/008* (2013.01); *B65B 57/10* (2013.01); *G01M 11/00* (2013.01); *G01N 21/3577* (2013.01); *G01N 21/90* (2013.01); *G01N 21/958* (2013.01); *G01V 8/12* (2013.01); *G01N 2021/9583* (2013.01)

(58) Field of Classification Search
CPC . G01N 21/64; G01N 21/3563; G01N 21/3577
See application file for complete search history.

(56) References Cited

U.S. PATENT DOCUMENTS 6,124,594 A      9/2000  Duggan
2002/0066867 A1* 6/2002  Ross, III ............... B65B 25/008
                                              250/461.1
2002/0125436 A1  9/2002  Muller

FOREIGN PATENT DOCUMENTS

EP           0999140 A1    5/2000

OTHER PUBLICATIONS

PCT International Search Report dated Dec. 14, 2015, International Application No. PCT/EP2015/070531, International Filing Date Sep. 9, 2015.

(Continued)

*Primary Examiner* — David Porta
*Assistant Examiner* — Faye Boosalis
(74) *Attorney, Agent, or Firm* — Robert A. Ambrose

(57) ABSTRACT

A method for detecting the presence or absence of an ophthalmic lens (10), in particular of a contact lens, within a receptacle (1), including the steps of:

detecting infrared radiation coming from at least a portion (3) of the receptacle (1) where the ophthalmic lens (10) is supposedly accommodated, analyzing the detected infrared radiation in a spectral portion in which absorbance ($A_L$) of a material the ophthalmic lens is made of is significantly different from absorbance ($A_R$) of a material the receptacle is made of, and from the analysis of the spectral portion detecting the presence or absence of the ophthalmic lens (10) within the receptacle.

16 Claims, 2 Drawing Sheets

(51) Int. Cl.
*G01M 11/00* (2006.01)
*G01N 21/958* (2006.01)
*G01N 21/90* (2006.01)

(56) References Cited

OTHER PUBLICATIONS

PCT Written Opinion of the International Searching Authority dated Dec. 14, 2015, International Application No. PCT/EP2015/070531, International Filing Date Sep. 9, 2015.

* cited by examiner

METHOD FOR DETECTING THE PRESENCE OR ABSENCE OF AN OPHTHALMIC LENS, IN PARTICULAR A CONTACT LENS, WITHIN A RECEPTACLE

This application claims the benefit under 35 USC §119(e) of U.S. provisional application Ser. No. 62/047,693 filed Sep. 9, 2014, incorporated herein by reference in its entirety.

FIELD

The invention relates to a method for detecting the presence or absence of an ophthalmic lens, in particular a contact lens, within a receptacle. The invention also relates to a lens detection station for detecting the presence or absence of an ophthalmic lens, in particular a contact lens, within a receptacle.

BACKGROUND

Ophthalmic lenses, in particular contact lenses, are nowadays produced in great volumes in highly automated manufacturing lines. In a packaging station of such manufacturing line the contact lens is placed into a receptacle for the final contact lens packaging. Usually saline is added into the receptacle and a removable cover is placed, for example laminated, on top of the receptacle to provide for a liquid-tight closure of the receptacle containing the contact lens in the saline for the storage and shipment of the package.

In a final detection step it is ascertained that actually one and only one contact lens is present in the receptacle of the contact lens package. One method for detecting whether or not one contact lens and only one contact lens is present within a receptacle is based on fluorescence. In this method, the translucent receptacle is irradiated with ultraviolet radiation stimulating the contact lens material to emit fluorescent light. By detecting the amount of fluorescent light coming from within the receptacle it may be concluded whether or not a contact lens is present within the receptacle. From the amount of detected fluorescent light it may also be concluded if more than one contact lens is contained within the receptacle.

The ultraviolet radiation for the stimulation of fluorescence of the contact lens material has a wavelength smaller than 300 nm. Ultraviolet light sources which emit radiation of wavelengths smaller than 300 nm only have a limited lifetime, which in the case of usually employed UV-LEDs may amount to only some hundred hours. Thus, the ultraviolet light sources must be replaced comparatively frequently, which may interfere with the automated manufacturing process and reduces the efficiency of the manufacturing process. In addition, in order to protect the operating personnel from any irritation caused by the ultraviolet radiation reliable shielding measures must be provided. However, such shielding measures may present a physical obstacle both to the operational procedures and the operating personnel, and leads to an increase of the costs of the manufacturing process. In addition, the method for detection of the contact lens based on fluorescence depends strongly on the material the contact lens is made of. Depending on the lens material, a detection based on fluorescence may not be an option.

It is therefore an object of the invention to provide a method for the detection of an ophthalmic lens, in particular a contact lens within a receptacle which avoids the aforementioned disadvantages and which is technically simple and reliable.

SUMMARY

To achieve this, in accordance with one aspect of the present invention a method for detecting the presence or absence of an ophthalmic lens, in particular a contact lens, within a receptacle, is suggested. The method according to the invention comprises the steps of:

detecting infrared radiation coming from at least one portion of said receptacle where said ophthalmic lens is supposedly accommodated, analyzing said detected infrared radiation in a spectral portion in which absorbance of a material said ophthalmic lens is made of is significantly different from absorbance of a material said receptacle is made of, and from said analysis of said spectral portion detecting the presence or absence of a said ophthalmic lens within said receptacle.

In accordance with one aspect of the method according to the invention said step of detecting infrared radiation comprises detecting infrared radiation in a wavelength range of about 6.6 µm to about 10 µm.

In accordance with a further aspect of the method according to the invention detecting infrared radiation in said wavelength range of about 6.6 µm to about 10 µm is performed using a filter which is permeable in said wavelength range of about 6.6 µm to about 10 µm.

In accordance with still a further aspect of the method according to the invention said step of detecting said infrared radiation is performed using an infrared sensor.

In accordance with yet a further aspect of the method according to the invention said step of detecting said infrared radiation is performed using an infrared camera.

In accordance with a further aspect of the method according to the invention said step of detecting said infrared radiation coming from at least a portion of said receptacle is performed from beneath a bottom of said receptacle.

Alternatively or in addition, in accordance with yet a further aspect of the method according to the invention said step of detecting said infrared radiation is performed from a lateral side of said receptacle.

According to yet a further aspect of the method according to the invention said step of detecting said infrared radiation is performed with said receptacle being filled with a liquid.

In accordance with still a further aspect of the method according to the invention said receptacle is part of a contact lens package comprising said receptacle and a removable cover which is attached to a top surface of said receptacle, and said step of detecting said infrared radiation is performed with said removable cover being attached to said top surface of said receptacle.

In accordance with a further aspect of the method according to the invention said step of detecting said infrared radiation is performed by detecting said infrared radiation coming from said whole receptacle.

In accordance with a further aspect of the method according to the invention said receptacle is illuminated by ambient light only.

Yet in accordance with a further aspect of the method according to the invention said absorbance of said material said ophthalmic lens is made of is more than 2% higher than said absorbance of said material said receptacle is made of, preferably more than 5% higher than said absorbance of said material said receptacle is made of and, if applicable, more than 10% higher than said absorbance of said liquid, preferably more than 15% higher than said absorbance of said liquid.

Another aspect of the invention relates to a lens detection station for detecting the presence or absence of an ophthalmic lens, in particular a contact lens, in a receptacle. The lens detection station comprises a detector adapted and arranged to detect infrared radiation coming from at least a portion of said receptacle where said ophthalmic lens is supposedly accommodated, said detector further being adapted for said detected infrared radiation in a spectral portion in which absorbance of a material said ophthalmic lens is made of is significantly different from absorbance of a material said ophthalmic lens is made of. Said detector is further adapted for detecting from said analysis of said spectral portion the presence or absence of a said ophthalmic lens within said receptacle.

In accordance with one aspect of the lens detection station according to the invention said detector is adapted for detecting said infrared radiation in a wavelength range of 6.6 µm to 10 µm.

In accordance with a further aspect of the lens detection station according to the invention, said detector is an infrared camera.

Generally, the invention makes use of the fact that the materials ophthalmic lenses, in particular contact lenses, are made of have typical absorption characteristics with regard to infrared radiation. Accordingly, infrared radiation coming from the receptacle supposedly accommodating the contact lens may be detected and analyzed for an absorption spectrum which is typical for the respective lens material. In particular, the detection method is a passive detection method and does not require irradiation of the contact lens with ultraviolet radiation for stimulating fluorescence. Generally, the method according to the invention does not require any irradiation of the contact lens at all (ambient light may be sufficient). Costly and relatively short-lived sources for ultraviolet radiation can thus be omitted. Also, due to the absence of an ultraviolet radiation source there is no more need for a shielding of the operating personnel against ultraviolet radiation. Thus, the drawbacks of providing such shielding do no longer exist, either. The method according to the invention is capable of distinguishing whether or not a lens is present within the receptacle; it is also capable of detecting the presence of more than one lens within the receptacle.

According to Wien's displacement law the wavelength distribution of thermal radiation from a black body at any temperature has essentially the same shape as the distribution at any other temperature. From this general law it follows that there is an inverse relationship between the wavelength of the peak of the emission of a black body and its temperature, when expressed as a function of wavelength. Thus, according to Wien's displacement law the wavelength at which the intensity of emitted radiation has its maximum may be expressed as $\lambda_{max}=2897.8$ µm·K/T, in which K means Kelvin and T stands for the absolute temperature in Kelvin. In particular, the range of wavelengths between 6.6 µm and 10 µm corresponds to temperatures in the range of about 17° C. to about 166° C. Materials commonly used for the manufacture of ophthalmic lenses, in particular contact lenses, have absorbance peaks within the specified wavelength range, so that a reliable identification of a lens within the receptacle, using infrared detection may be ascertained. However, materials from which the receptacles for the contact lenses are made, for example polypropylene, have absorbance peaks within this wavelength range, too. Therefore, the detected infrared radiation is analyzed in a spectral portion where the absorbance of the material the contact lens is made of is significantly different from the absorbance of the material the receptacle is made of. The term "significantly different" is to be understood in a sense such that the absorbance of the material the contact lens is made of is different from the absorbance of the material the receptacle is made of is at least 2%, preferably more than 5%. Thus, the contrast between the receptacle and the contact lens can be increased and detection can be improved. Preferably, the detected infrared radiation is analyzed in a spectral portion in which absorbance of the material the contact lens is made of is high while the material the receptacle is made of has only little absorbance.

Detecting the infrared radiation in the wavelength range of about 6.6 µm to about 10 µm may be performed using a filter which is permeable in said wavelength range only. For example, the filter may be placed between the receptacle and a detector, for example an infrared sensor or an infrared camera, or the filter may be part of the detector itself.

For example, the infrared sensor may be scanned across that portion of the receptacle where the contact lens is supposedly accommodated in order to determine whether or not a lens is present within the receptacle and in order to identify if more than one lens is present. In case the infrared sensor has a large enough infrared sensitive surface (such as in the case of a suitable infrared camera), the infrared radiation coming from the whole receptacle can be analyzed simultaneously. A suitable infrared camera may be, for example, a camera of the type "thermoIMAGER TIM 640" available from the company Micro-Epsilon Messtechnik, Ortenburg, Germany.

Detection of the infrared radiation can be performed from beneath a bottom of the receptacle. However, alternatively or in addition thereto, detection may be performed from a lateral side of the receptacle. Detection from a lateral side may be of particular advantage for the detection of more than one lens within the receptacle.

The method according to the invention even allows detection of the presence or absence of a contact lens in an already closed contact lens package comprising a receptacle and a removable cover which is attached to a top surface of the receptacle. The receptacle may even be filled with a liquid, for example saline. As already mentioned, for obtaining a high contrast between the contact lens on one hand and the receptacle and the liquid on the other hand, the analyzed spectral portion of the detected infrared radiation is selected such that the absorbance of the material the receptacle is made of and the absorbance of the saline (or another suitable liquid like water) on one hand are both significantly different from the absorbance the material is made of. Preferably, absorbance of the material the contact lens is made of is high while the material the receptacle is made of and the saline both have only little absorbance. As already mentioned, the method according to invention does not require a special light source. Thus, detection may be performed under ambient light.

The lens detection station of the invention is advantageous for the same reasons as it the above-discussed method. Therefore, the advantages are not reiterated here.

BRIEF DESCRIPTION OF THE DRAWINGS

Further details and advantages of the invention will become apparent from the following description of an exemplary embodiment thereof, reference being made to the schematic drawings, in which.

DETAILED DESCRIPTION OF EMBODIMENTS

Figure 1:
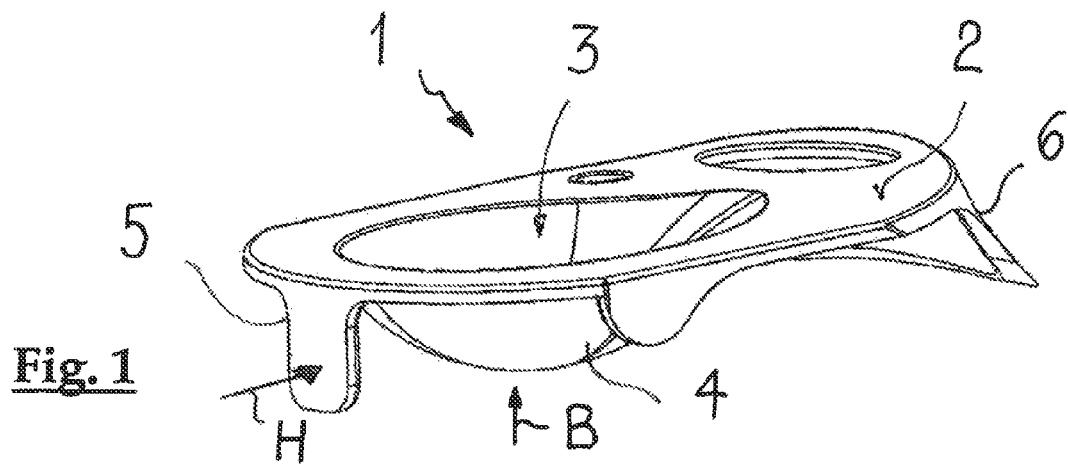
FIG. 1 shows a perspective view of a contact lens package.

FIG. 1 shows an exemplary embodiment of a receptacle 1 of a contact lens package. Such contact lens package usually comprises the receptacle 1 and a closure, which usually is attached, for example laminated (in case of a foil), to a top surface 2 of the receptacle 1. As the closure is of no specific importance to the invention, it is not shown in the drawings, as detection of the presence or absence of the contact lens can be performed with or without closure. The receptacle 1 is provided with a concavely shaped cavity 3, in which a contact lens is to be accommodated. Corresponding to the concavely shaped cavity 3, the receptacle 1 may have a convexly curved bottom 4. Supporting flanges 5 and 6, which extend at the sides of the receptacle 1 towards the bottom 4 thereof, facilitate a stable placement of the receptacle 1 on a supporting surface. The receptacle 1 may be made of polypropylene, for example. In a packaging station of an automated contact lens manufacturing line, a contact lens is placed into the concavely shaped cavity 3 of the receptacle 1 which is subsequently filled with a liquid, such as water or saline.

In order to be able to detect whether or not a contact lens is present within the cavity 3 of the receptacle 1 a detector which is sensitive to infrared radiation may be arranged in a lens detection station in order to observe the receptacle 1 as a whole or at least a portion thereof which comprises the cavity 3. The detector may be embodied as or comprise an infrared sensor or an infrared camera. In FIG. 1 the directions from which the detector may observe the receptacle 1 are indicated with arrows B and H, respectively. Arrow B indicates that the detector observes the receptacle 1 from beneath the receptacle 1 (i.e. the detector is arranged beneath the bottom 4 of the receptacle). Arrow H indicates that the detector observes the receptacle 1 from a lateral side of the receptacle 1 (in the embodiment shown from about horizontally; i.e. the detector is arranged at a lateral side thereof).

Figure 2:
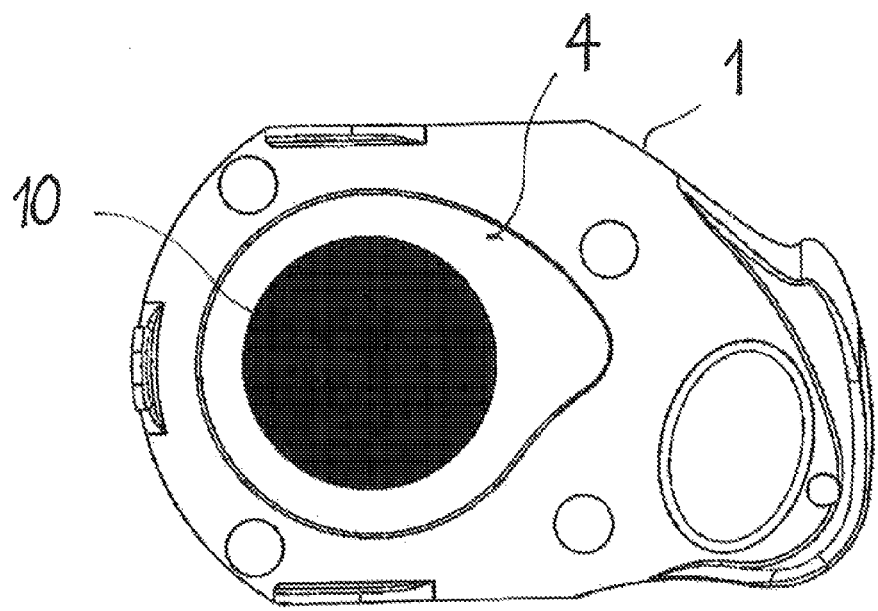
FIG. 2 shows an image of a contact lens package containing a contact lens within the receptacle, obtained with an infrared camera arranged beneath the bottom of the receptacle.

FIG. 2 shows schematically an image obtained with an infrared camera which is arranged beneath the bottom 4 of the receptacle 1, such that the receptacle 1 is observed from underneath. The outlines of the receptacle 1 and its cavity 3 are clearly visible. A contact lens 10 within the cavity 3 of the receptacle 1 is shown in black contrast, corresponding to the absorption of infrared radiation by the material the contact lens is made of, as detected by the infrared camera.

Figure 3:
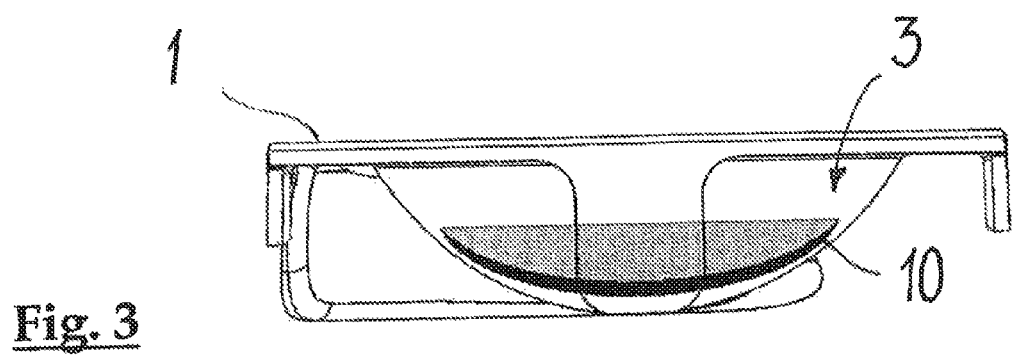
FIG. 3 shows an image of a contact lens package containing a contact lens within the receptacle, obtained with an infrared camera arranged at a lateral side of the receptacle.

FIG. 3 shows an image from an infrared camera which is arranged at a lateral side of the receptacle (about horizontally relative to the receptacle) such that the receptacle 1 is observed from laterally. Again, the outlines of the receptacle 1 are clearly visible. The contact lens 10 is shown in shades ranging from black to grey. This is a result of the different amounts of absorption of infrared radiation, which is dependent from the length of travel of the infrared radiation through the material of the contact lens 10 within the cavity 3 of the receptacle 1. The observation from a lateral side of the receptacle 1 also may provide clear information as to whether more than one contact lens is present within the receptacle 1.

Figure 4:
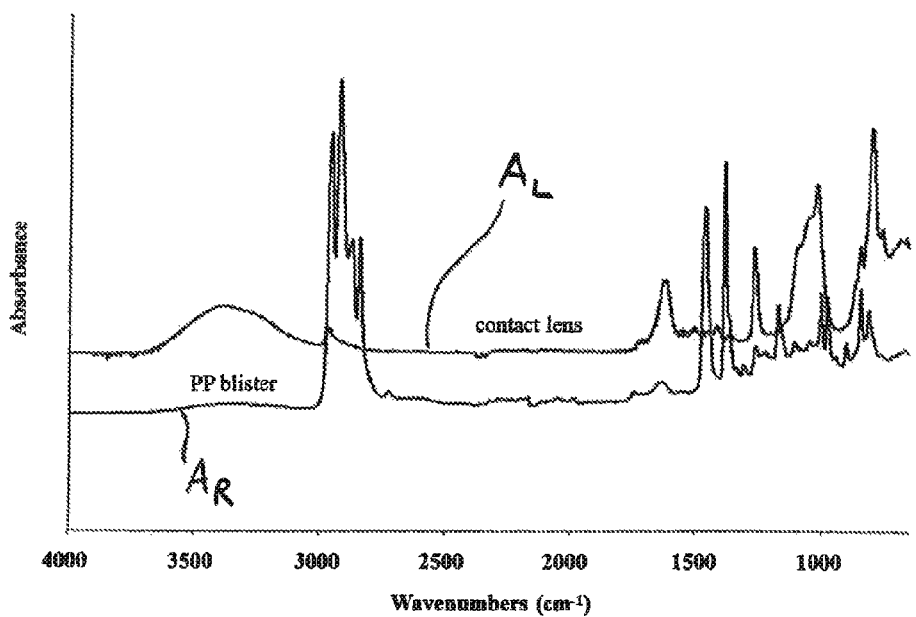
FIG. 4 shows graphs representing the absorbance of a contact lens made of a silicone hydrogel material and of a receptacle made of polypropylene.

The diagram in FIG. 4 shows two graphs representing the absorbance $A_R$ of a receptacle made of polypropylene and the absorbance $A_L$ of a contact lens made of a silicone hydrogel material such as from a material obtained from a mixture of the following substances, with "% (w/w)" indicating the weight percentage per total weight:

| | |
|---|---|
| Chain-Extended Polydimethylsiloxane (CE-PDMS) | 31.83% (w/w) |
| 3-acrylamidopropoyl (trimethyl-siloxy) silane (TRIS-AAm) | 20.71% (w/w) |
| 1-propanol (1PrOH) | 21.72% (w/w) |
| N,N-Dimethyl acrylamide (DMA) | 23.24% (w/w) |
| 2-Hydroxy-2-Methyl-1-Phenyl-1-Propanone (Darocur 1173) | 1.01% (w/w) |
| N-(carbonyl-methoxyethylene glycol 2000)-1,2distearoyl-sn-Glycerol-3-phosphoethanolamine, sodium salt (L-PEG 2000) | 0.61% (w/w) |
| 1,2-Dimyristoyl-sn-glycero-3-phosphorylcholine (DMPC) | 0.76% (w/w) |
| 4-Hydroxy-2,2,6,6-tetramethyl-piperidine-1-oxyl (H-Tempo) | 0.02% (w/w) |
| 3-Methacryloxypropyl-tris-(trimethylsiloxy) silane (TRIS) Copper Phthalocyanine (CuP) Suspension (Source Batch) (Visitint Dispersion) | 0.10% (w/w) |

On the abscissa wavenumbers are shown (unit: $cm^{-1}$) while the ordinate shows the absorbance at the respective wavelength (unit: %). No absolute numbers and dimensions are specified on the ordinate, since they depend on the specific detector used, from the amplification factor in the electronics in the respective wavelength range, etc. In any event, the difference in absorptions is sufficient to reliably detect the presence or absence of a contact lens in the cavity 3 of the receptacle 1. The respective wavenumber on the abscissa corresponds to the reciprocal of the wavelength (=$1/\lambda$). The two graphs in FIG. 4 show that the receptacle made of polypropylene has peaks of the absorbance in a different wavelength range than the material the contact lens is made of. Thus, in the analysis of the detected infrared radiation the two materials can be reliably distinguished. For example, in the embodiment shown a first wavenumber range of 1300 $cm^{-1}$ to 1210 $cm^{-1}$ (corresponding to a wavelength range of 7.7 μm to 8.3 μm) and a second wavenumber range of 1150 $cm^{-1}$ to 1000 $cm^{-1}$ (corresponding to a wavelength range of 8.7 μm to 10 μm) are particularly advantageous, since in these ranges the absorbance $A_L$ of the contact lens and the absorbance $A_R$ of the polypropylene receptacle are significantly different so that a reliable detection of the contact lens can be performed.

Figure 5:
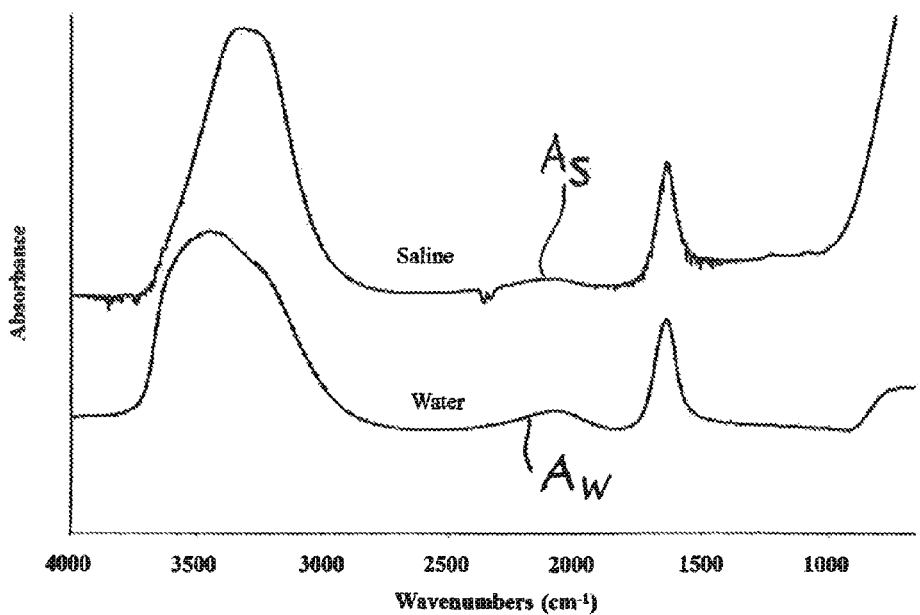
FIG. 5 shows graphs representing the absorbance of water and of a saline.

The graphs shown in the diagram of FIG. 5 shows the absorbance $A_W$ of water and the absorbance $A_S$ of a saline, respectively. Again, on the abscissa wavenumbers are shown while the ordinate shows the absorption at the respective wavelength in %. The two graphs representing the respective absorbance $A_W$ and $A_S$ are very similar to each other and have peaks in the absorbance practically in the same wavelength range.

A comparison of the absorbance $A_R$, $A_L$, $A_W$ and $A_S$ represented by the graphs shown in FIG. 4 and FIG. 5 shows that the absorbance $A_L$ of the contact lens has maxima in a wavenumber range (wavelength range) which is clearly distinct from the maxima in absorbance $A_R$, $A_W$ and $A_S$ of the polypropylene receptacle and of water and saline, respectively. Thus, the passive detection method employing a detector for detecting infrared radiation and for the analysis of the detected infrared radiation may lead to clear and unambiguous results as to whether or not a contact lens is accommodated within the receptacle, and as to whether or not more than one contact lens is present within the receptacle. The detection method may be performed even with contact lens packages in which the receptacle has been loaded with a contact lens and has been filled with water or saline, and after the receptacle has been provided with a removable closure (for example a foil), which may have been attached, for example laminated, to a top surface of the receptacle. However, detection may also be performed when the receptacle has been loaded with a contact lens but before water or saline have been added, or after water or saline have been added but before the foil has been attached to the receptacle.

Although the invention has been described with the aid of a specific embodiment, it is evident to the person skilled in the art that this embodiment has been described by way of example only while it represents a more general teaching, and that various changes and modifications are conceivable without departing from this general teaching underlying the invention. Therefore, the scope of protection is not intended to be limited by the embodiment described, but rather is defined by the appended claims.

What is claimed is:

1. A method for detecting the presence or absence of an ophthalmic lens (10) within a receptacle (1), the method comprising the steps of:
    detecting infrared radiation coming from at least a portion (3) of said receptacle (1) where said ophthalmic lens (10) is supposedly accommodated,
    analyzing said detected infrared radiation in a spectral portion in which absorbance (AL) of a material said ophthalmic lens (10) is made of is significantly different from absorbance (AR) of a material said receptacle (1) is made of, and
    from said analysis of said spectral portion detecting the presence or absence of a said ophthalmic lens (10) within said receptacle (1);
        wherein said step of detecting infrared radiation comprises detecting infrared radiation in a wavelength range of about 6.6 µm to about 10 µm; and
        wherein said receptacle (1) is illuminated by ambient light only.

2. The method of claim 1, wherein detecting infrared radiation in said wavelength range of about 6.6 µm to about 10 µm is performed using a filter which is permeable in said wavelength range of about 6.6 µm to about 10 µm.

3. The method of claim 2, wherein said step of detecting said infrared radiation is performed using an infrared sensor.

4. The method of claim 3, wherein said step of detecting said infrared radiation is performed using an infrared camera.

5. The method of claim 2, wherein said absorbance (AL) of said material said ophthalmic lens (10) is made of is more than 2% higher than said absorbance (AR) of said material said receptacle (1) is made of, and more than 10% higher than said absorbance (AW, AS) of said liquid.

6. The method of claim 1, wherein said step of detecting said infrared radiation is performed from beneath a bottom (4) of said receptacle (1).

7. The method of claim 1, wherein said step of detecting said infrared radiation is performed from a lateral side of said receptacle (1).

8. The method of claim 1, wherein said step of detecting said infrared radiation is performed with said receptacle being filled with a liquid.

9. The method of claim 1, wherein said receptacle (1) is part of a contact lens package comprising said receptacle (1) and a removable cover which is attached to a top surface (2) of said receptacle (1), and wherein said step of detecting said infrared radiation is performed with said removable cover being attached to said top surface (2) of said receptacle (1).

10. The method of claim 1, wherein said step of detecting said infrared radiation coming from at least a portion of said receptacle (1) is performed by detecting said infrared radiation coming from said whole receptacle (1).

11. The method of claim 1, wherein said step of detecting infrared radiation comprises detecting infrared radiation in a wavelength range of about 6.6 µm to about 8.3 µm.

12. The method of claim 1, wherein said step of detecting infrared radiation comprises detecting infrared radiation in a wavelength range of about 7.7 µm to about 8.3 µm.

13. The method of claim 1, wherein said step of detecting infrared radiation comprises detecting infrared radiation in a wavelength range of about 8.7 µm to about 10 µm.

14. A lens detection station for detecting the presence or absence of an ophthalmic lens (10) in a receptacle (1), the lens detection station comprising a detector adapted and arranged to detect infrared radiation coming from at least a portion (3) of said receptacle (1) where said ophthalmic lens (10) is supposedly accommodated, said detector further being adapted for analyzing said detected infrared radiation in a spectral portion in which absorbance (AL) of a material said ophthalmic lens (10) is made of is significantly different from absorbance (AR) of a material said receptacle is made of, and said detector further being adapted for detecting from said analysis of said spectral portion the presence or absence of a said ophthalmic lens (10) within said receptacle (1); and
    wherein said detector is adapted for detecting said infrared radiation in ambient light only and in a wavelength range of about 6.6 µm to about 10 µm.

15. The lens detection station of claim 14, wherein said detector is an infrared camera.

16. The lens detection station of claim 14, comprising a filter which is permeable in said wavelength range of about 6.6 µm to about 8.3 µm, or is permeable in said wavelength range of about 8.7 µm to about 10 µm.

* * * * *